United States Patent [19]
Gaeng et al.

[11] Patent Number: 5,151,523
[45] Date of Patent: Sep. 29, 1992

[54] PREPARATION OF 2-METHYLBENZOXAZOLE

[75] Inventors: Manfred Gaeng, Bobenheim-Roxheim; Heinz Saukel, Friedelsheim; Wolfgang Hoffmann, Frankenthal; Josef Koenig, Zellertal, all of Fed. Rep. of Germany

[73] Assignee: BASF Aktiengesellschaft, Ludwigshafen, Fed. Rep. of Germany

[21] Appl. No.: 667,111

[22] Filed: Mar. 11, 1991

[30] Foreign Application Priority Data

Mar. 21, 1990 [DE] Fed. Rep. of Germany ....... 4009027

[51] Int. Cl.⁵ .......................................... C07D 263/56
[52] U.S. Cl. .................................................. 548/217
[58] Field of Search ............................................ 548/217

[56] References Cited

U.S. PATENT DOCUMENTS

| | | | |
|---|---|---|---|
| 1,745,843 | 2/1930 | Clarke | 548/217 |
| 2,746,971 | 5/1956 | Dortou | 548/217 |
| 2,910,472 | 10/1959 | Siegrist et al. | 548/217 |
| 3,158,610 | 11/1964 | Buell | 548/217 |
| 3,452,030 | 6/1969 | Crocker | 548/217 |
| 3,786,064 | 1/1974 | Harnisch | 548/217 |
| 3,880,661 | 4/1975 | Lau | 430/385 |
| 3,985,755 | 10/1976 | Narayanan | 548/217 |
| 4,025,637 | 5/1977 | Dunwell | 548/217 |
| 4,743,595 | 5/1988 | Itoh | 548/217 |

FOREIGN PATENT DOCUMENTS

| | | | |
|---|---|---|---|
| 0031296 | 7/1981 | European Pat. Off. | 548/217 |
| 2292270 | 12/1990 | Japan | 548/217 |

*Primary Examiner*—Donald G. Daus
*Attorney, Agent, or Firm*—Keil & Weinkauf

[57] ABSTRACT

A process for preparing 2-methylbenzoxazole by cyclizing acetamidophenol with the simultaneous elimination of the water of reaction. The process involves the drying and melting of the acetamidophenol, the cyclization of acetamidophenol to 2-methylbenzoxazole, and the removal of the water of reaction and the 2-methylbenzoxazole from the reaction mixture after the cyclization step by distillation. All the steps are carried out in a dryer.

3 Claims, 1 Drawing Sheet

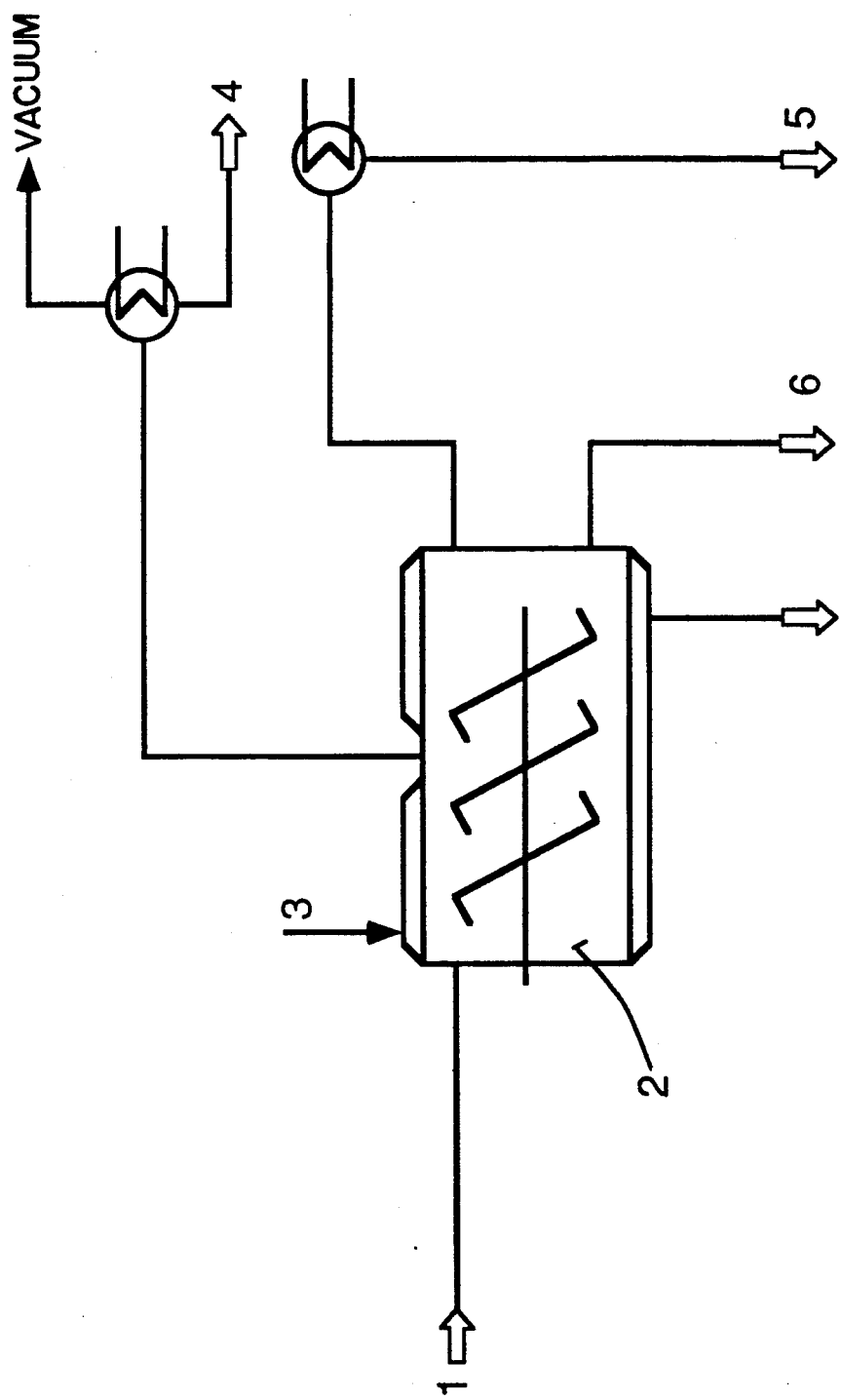

PREPARATION OF 2-METHYLBENZOXAZOLE

The present invention relates to a process for preparing 2-methylbenzoxazole by cyclizing acetamidophenol in the presence of PLURIOL 400E with simultaneous elimination of water. PLURIOL 400E is a colorless, clear liquid which is a mixture of polyethylene glycols and has the general formula $HO(CH_2CH_2O)_nH$.

The reaction takes place in accordance with the following equation:

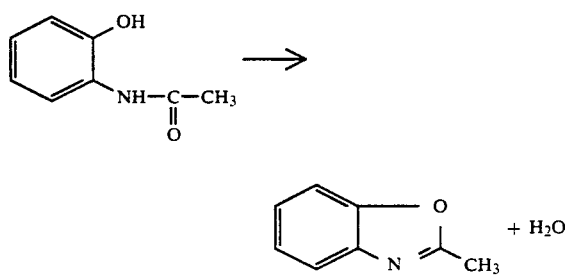

The prior art preparation of 2-methylbenzoxazole is as follows:

2400kg of acetamidophenol+(3000 kg of $H_2O$+230 kg of PLURIOL 400E) →1720 kg of 2-methylbenzoxazole+394 kg of residue+286 kg of $H_2O$+(3000 kg of $H_2O$+230 kg of PLURIOL 400E)

This corresponds to a conversion of acetamidophenol into 2-methylbenzoxazole of about 72%.

This reaction is carried out in a stirred container at about 160°–170° C. with subsequent removal of water and 2-methylbenzoxazole from the reaction mixture by distillation. Acetamidophenol is added to the reaction as dried product.

The disadvantages of the process are that, as is evident from the balance of amounts, the conversion is only about 72%, the residue and PLURIOL 400E have to be disposed of together with water, and the acetamidophenol must be dried in a separate apparatus.

It is an object of the present invention to design a process for preparing 2-methylbenzoxazole in which the conversion of acetamidophenol into 2-methylbenzoxazole is improved, ie. the yield of the process is increased, it is unnecessary to use PLURIOL 400E in the reaction, and thus the disposal problem can be reduced, and, finally, no separate apparatus is required for drying the acetamidophenol.

The latter means that the acetamidophenol is subjected to the cyclization in the state, namely wet, in which it is obtained in the preceding process stage.

We have found that this object is achieved by the drying and melting of the acetamidophenol, the cyclization thereof and the removal of the water of reaction and the 2-methylbenzoxazole from the reaction mixture after the cyclization by distillation being carried out in a dryer.

One example of the novel process with the essential features is depicted in the drawing and is described in detail hereinafter.

The drawing shows a simplified process diagram.

Acetamidophenol 1 (a filtercake wet with water as obtained in the preceding process stage) is fed into a dryer 2, for example a commercial paddle dryer. This paddle dryer has, in particular, a large heat-exchange area related to the volume. The following process steps are carried out successively in the paddle dryer with heat provided by a heat-transfer agent 3:

drying of the filtercake which is wet with water, melting the dried filtercake and simultaneously cyclizing the acetamidophenol to 2-methylbenzoxazole with elimination of water of reaction, removal of the water of reaction 4 by distillation during the cyclization, starting at atmospheric pressure and then during the course of the cyclization under reduced pressure to diminish the formation of residue and, after removal of the water of reaction by distillation, removal of the 2-methylbenzoxazole 5 by distillation and subsequently removal of the residue 6 from the paddle dryer.

The described process has been shown to have distinct advantages over the prior art process, namely yield increased from about 72% to about 78–80%, PLURIOL 400E not used, reduced formation of products which must be disposed of, reduction in the investment costs in the design of a new plant, and omission of the handling of dried acetamidophenol, which was desirable for safety reasons.

We claim:

1. In the process of preparing 2-methylbenzoxazole by the cyclization of acetamidophenol, the improvement consisting essentially of:

preparing a filtercake of acetamidophenol which is wet with water;

feeding the wet filtercake into a dryer;

drying the filtercake;

melting the dried filtercake;

simultaneously with the melting step, cyclizing the acetamidophenol to 2-methylbenzoxazole with the elimination of water of reaction;

removing the water of reaction by distillation during the cyclization step, starting at atmospheric pressure and reducing the pressure during the cyclization step;

removing the formed 2-methylbenzoxazole by distillation to leave a residue; and removing the residue from the dryer.

2. The process of claim 1 wherein the dryer is a paddle dryer.

3. The process of claim 1 wherein the dryer is a discotherm dryer.

* * * * *